(12) United States Patent
McCarthy

(10) Patent No.: US 7,744,682 B2
(45) Date of Patent: Jun. 29, 2010

(54) MULTI-CHAMBER AIR STERILIZATION SYSTEM AND METHOD

(76) Inventor: Walton W. McCarthy, 117 Cole St., Forney, TX (US) 75126

( * ) Notice: Subject to any disclaimer, the term of this patent is extended or adjusted under 35 U.S.C. 154(b) by 0 days.

(21) Appl. No.: 11/373,447

(22) Filed: Mar. 11, 2006

(65) Prior Publication Data

US 2008/0141864 A1 Jun. 19, 2008

(51) Int. Cl.
*B01D 47/00* (2006.01)

(52) U.S. Cl. .................... 96/224; 422/24; 422/186.3

(58) Field of Classification Search ................ 96/224, 96/413, 417; 422/24, 186.6, 186
See application file for complete search history.

(56) References Cited

U.S. PATENT DOCUMENTS

| 6,221,314 | B1 * | 4/2001 | Bigelow ................. 422/24 |
|---|---|---|---|
| 6,296,693 | B1 * | 10/2001 | McCarthy ................. 96/117.5 |
| 6,766,097 | B2 * | 7/2004 | Horton, III ................. 385/147 |
| 6,797,966 | B2 * | 9/2004 | Summers et al. ......... 250/492.1 |
| 6,949,223 | B2 * | 9/2005 | McEllen ..................... 422/120 |
| 7,048,776 | B2 * | 5/2006 | Moore et al. ..................... 95/8 |
| 7,326,387 | B2 * | 2/2008 | Arts et al. ................ 422/186.3 |
| 2003/0021721 | A1 * | 1/2003 | Hall ............................. 422/4 |

* cited by examiner

*Primary Examiner*—Duane Smith
*Assistant Examiner*—Sonji Turner
(74) *Attorney, Agent, or Firm*—Michael J. Persson; Lawson & Persson, PC

(57) ABSTRACT

A multi-chamber air sterilization system including an air inlet, an air test chamber in fluid communication with the air inlet, a mechanical and chemical filtration chamber, an ultraviolet light chamber, a blower and an air exhaust. The system includes a filter sleeve for filtering particulates and chemical agents, and an ultraviolet lamp for killing biological agents.

19 Claims, 3 Drawing Sheets

MULTI-CHAMBER AIR STERILIZATION SYSTEM AND METHOD

FIELD OF THE INVENTION

The present invention relates to the field of disaster survival equipment and, in particular, to a multi-chamber air sterilization system and method that filters and sterilizes contaminated air entering a disaster shelter or room in the event of a disaster.

BACKGROUND OF THE INVENTION

In spite of a large amount of misinformation which has been presented to the public, there is convincing scientific and technical information available that it is possible for most people to survive a full scale exchange of nuclear, biological or chemical weapons, or disaster caused by an industrial accident provided that proper advance preparations are made.

It is acknowledged that there would be little incentive for an individual to survive such a nuclear holocaust or biological disaster if, as a result, all life on earth were doomed to extinction or marginal existence. However, the National Academy of Sciences (NAS) has produced extensive reports on the atmospheric effects from various war scenarios, which contradict any such idea. In reality, therefore, the question today is not whether persons can survive a nuclear, biological and chemical warfare or disaster agents, but whether people have the will and determination to prepare for survival.

A number of underground disaster shelters have been developed in preparation of such a disaster. The typical backyard, or personal, shelter has the capability of providing shelter for a small number of people, such as a family unit and incorporates features to protect its occupants against some of the effects of nuclear weapons. However, many shelters have oxygen tanks to provide the shelterists with fresh, uncontaminated air. Further, even in shelters that do include liquid oxygen tanks, these tanks are seldom large enough to provide sufficient oxygen to such a shelter for extended periods of time. Therefore, when oxygen tanks are depleted, or malfunction, shelterists are forced to breath air from outside the shelter, which may be contaminated by a number of different agents. Therefore, there is a need to provide an air sterilization system that will purify contaminated air entering a disaster shelter.

It is recognized that a number of air purification systems have been designed to filter the air in a room in order to remove contaminants from breathable air. For example, U.S. Pat. No. 5,207,877 issued May 3, 1993, describes a method for the purification of air in which air polluted with potentially harmful chemical and biological matter is purified and pollutants degraded to less hazardous substances by a combined chemical and electrical process.

Although this invention purifies and destroys most potentially harmful airborne chemicals, microorganisms and other biologicals both by chemical and electrochemical means, it has a number of drawbacks. First, the system does not filter harmful nuclear fallout, and therefore is ineffective in the event of a nuclear disaster. Second, it is directed at purifying the air in a room where a known contaminant is found and therefore, neither filters incoming air nor maintains a closed environment to prevent outside air from entering a room. Third, the electrochemical reaction utilized by this system relies on available ions and bondable compounds to attract the hazardous and undesirable contaminants. Accordingly, this method will eventually cease to function properly due to the lack of available bondable ions and compounds. In such an event, the filtration system will not function properly unless the used chemicals are removed and fresh chemical replenished. Finally, the need to remove and replenish chemicals creates another potential hazard for the average person due to the risk of accidents during handling and storage of the spent and unspent chemical. For these reasons this method of air purification is not suitable for use in protecting from nuclear, biological and chemical disasters.

U.S. Pat. No. 4,337,071 issued Jun. 29, 1982 describes an on-site apparatus that produces cryogenic temperatures used to remove, by condensations all pollutants in the air so that an ultra clean air supply is obtained for human consumption in the interior of living enclosures, such as automobiles, homes, offices, hospitals etc. The apparatus can recycle air in the enclosure, i.e. resupply the oxygen consumed by the human being and remove the carbon dioxide produced by respiration. Cold traps (filters) of different cryogenic temperatures are built into the system to condense the pollutants of different condensation temperatures. The condensed pollutants can be disposed of by periodical defrost and purge of the system.

Although this system would allow a sealed room to maintain breathable atmosphere, it also has a number of drawbacks. First, this system does not contain a filter capable of removing nuclear fallout, biological hazards and dangerous chemicals from the air. Second, this system maintains a closed environment by recycling air, the system does not accomplish the decontamination process which is crucial for maintaining a safe environment in the event of a full scale exchange of nuclear, biological or chemical weapons, or disaster caused by an industrial accident. Third, the large amount of power required to maintain the temperatures required by these systems cannot be supplied for long by existing battery systems. Therefore, such a system will be ineffective in circumstances where power to a shelter is not functioning.

U.S. Pat. No. 5,626,820 issued May 6, 1997 describes a clean room air-filtering device. This device features a clean room and chemical air filter suitable for use in the air handling system of the clean room directly upstream of high-efficiency particulate air (HEPA) filters. This device includes a HEPA filter (high efficiency particulate air filter), in addition to chemical filters targeted for the removal of the specific contaminants contained in the various air streams inside a clean room. The clean room air filter is designed to remove chemicals and other gas-phase contaminants created from within the clean room itself during the regular activities occurring in the manufacture of semiconductor devices. In addition, this device includes a processing station that generates a gas-phase contaminant in which the activated carbon particles are preferably selected to remove contaminant produced by the processing station.

This system is also ill suited for use in disaster situations. First, this air handling system preferably includes a make-up air system for drawing air from an atmosphere outside of the clean room, and is subject to contamination by an ambient contaminant. As this make-up air is made to air is passed through borosilicate filter material, rather than more efficient HEPA and/or charcoal filters, this make-up air may act to contaminate the interior air. Second, as this filter is directed to preventing dust and other airborne contaminants from interfering with manufacturing operations, it is not suited for the protection of humans from nuclear fallout, chemical or biological disasters that occur outside the processing station. Finally, this system does not include any means of determining whether contaminants are present within the air entering the system and, therefore, would need to be continuously employed to be effective.

U.S. Pat. No. 5,399,319 issued Mar. 21, 1995 describes a portable, convertible apparatus for creating either a negative pressure or a positive pressure in and filtering the air in a room. Within the airflow path, a HEPA filter is located in the device. This device will maintain a negative pressure in a room thereby preventing the air from inside the room where the device is active from escaping the room. Allowing only non infected air from outside the room to enter the room where the device is located. Alternatively, the device can function to maintain clean air inside a room so that if a door in the room opens, clean air will rush out of the room thereby preventing contaminated air from rushing into the room.

Although this device is useful in creating either a positive or negative pressure inside a room and thus maintaining either the desired clean air or infected air inside a room, the device does not filter air from the outside. This device contains one filter, a HEPA filter, that is capable of removing small quantities of contaminants that accidental entered the room, but is not useful in removing contaminants from the air outside of the room, which is needed in order to filter air entering a shelter. This device does not take air directly from the atmosphere, or outside of the room, and filter contamination, rather the device filters only that air already present in the closed room. Therefore, it is not designed to maintain a clean air environment for an undefined period of time and provide adequate air for human survival. Finally, this device would not provide human protection from atmospheric contaminants in the event of a nuclear, biological or chemical attack or accident.

Finally, the inventor of the present invention invented the life cell disclosed and claimed in U.S. Pat. No. 6,296,693, which is directed at filtering contaminated air entering a room in the event of a disaster. This life cell includes a contaminant detector, for detecting the presence of a contaminant in a volume of air, and an air filtration system for removing contaminants from the volume of air. The air filtration system of the life cell includes an air inlet, HEPA filter in fluid communication with the air inlet for removing particulate contaminants from the volume of air, and a carbon filter in fluid connection with the HEPA filter for removing chemical and biological contaminants from the volume of air. A blower is placed in fluid communication with the carbon filter and HEPA filter and acts to draw the volume of air from the air inlet, through the HEPA filter and carbon filter, and exhaust the volume of air such that a positive pressure is created. The preferred life cell includes a carbon filter made up of two layers of foam, an activated carbon filter medium, and a Whetlerite carbon filter medium. Finally, the preferred life cell is disposed within a self-contained housing and includes a battery bank, a light, a radio, and a communications device.

The life cell disclosed in U.S. Pat. No. 6,296,693 is effective at filtering air entering a room of a home of most chemical and biological contaminants. However, because the life cell needed to create a positive pressure within a room, it could not be sealed to prevent ingress or egress of air from an enclosed space, like a shelter cell. In addition, the life cell did not protect against many strains of bacteria and airborne viruses. Finally, the two stage filtering design, where the HEPA filter and chemical filter were separated, increased the size of the life cell such that it could not easily fit within the entranceway of a conventional shelter. Therefore it does not solve all of the problems facing shelterists.

Therefore, there is a need for an air sterilization system that provides human protection from atmospheric contaminants in the event of a nuclear, biological or chemical attack or accident, that purifies air directly from the atmosphere, that may be effectively operated by batteries, that includes a means for determining whether contaminants are present within the air entering the system, that does not require that used chemicals are removed and fresh chemical replenished, that both purifies incoming air and exhausts spent air, heat and moisture from a shelter, that may be sealed to prevent ingress or egress of air from an enclosed space, and that protects against all known strains of bacteria and airborne viruses.

SUMMARY OF THE INVENTION

The present invention is an air sterilization system that meets the needs identified above. In its most basic form, the system includes an air inlet in communication with a source of air. An air test chamber is in fluid communication with the air inlet and a mechanical and chemical filtration chamber. The mechanical and chemical filtration chamber includes a filter sleeve made up of a highly effective particular air filter, an activated carbon layer, a chemical warfare agent filter layer and an outside filter layer manufactured of a material adapted to contain carbon fines within the filter sleeve. An ultraviolet light chamber is in communication with the mechanical and chemical filtration chamber. The ultraviolet light chamber includes an ultraviolet lamp disposed therein. Finally, an air blower in communication with the ultraviolet light chamber and an air exhaust in communication with the air blower and the interior of a shelter.

In operation, air is sucked into the system through the air inlet and into the air test chamber, where it may be tested for the presence of nuclear, chemical and/or biological agents. The air then passes into the mechanical and chemical filtration chamber, where it passes through the filter sleeve, effectively trapping all large particulates and chemically filtering chemical agents. The filtered air then passes through the ultraviolet light chamber where the ultraviolet lamp irradiates it with ultraviolet light to kill biological agents. The purified air the passes through the blower, where it blows through the air exhaust and into the shelter.

The preferred system includes a pre-filtering chamber disposed between the air inlet and the air test chamber. The preferred pre-filtering chamber includes a micronic screen manufactured of stainless steel through which air is forced to pass, although the micronic screens may be made from brass or non-metallic materials commonly used to filter larger particulates. The micronic screen is preferably removable and is accessed through a screen access port dimensioned to allow the micronic screen to be removed from the pre-filtering chamber. The preferred air test chamber includes a test port and a male plug dimensioned to mate with and be removable from the test port.

The preferred air sterilization system includes a filter sleeve that takes the form of a substantially hollow cylindrical shape having an open top and an open bottom. In the preferred embodiment, this is accomplished by using a top plate, a bottom plate, an acme rod secured to the bottom plate and passing through the top plate and filter sleeve, and a nut threaded onto the acme rod and in communication with said top plate. The filter sleeve includes a first gasket in communication with the top plate and a second gasket in communication with the bottom plate, and is sealably secured between the top plate and bottom plate by rotating the nut such that the acme rod and bottom plate move upward toward the top plate.

The highly effective particular air filter of the preferred filter sleeve is a pleated highly effective particular air filter. The chemical warfare agent filter layer of the filter sleeve preferably is manufactured at least in part of Whetlerite Carbon. The activated carbon filter layer of the filter sleeve preferably is manufactured both of activated carbon and impregnated carbon. Finally, the outside filter layer of the filter sleeve is preferably manufactured of a micronic fabric material adapted to contain carbon fines within the filter sleeve.

In the preferred air sterilization system, the ultraviolet lamp is an ultraviolet germicidal irradiation lamp adapted to generate ultraviolet light having a wavelength of 254 nanometers. The preferred ultraviolet lamp is dimensioned to slow the air flow as it flows through the ultraviolet light chamber such that the air is exposed to level of kill energy sufficient to kill substantially all biological agents. The preferred ultraviolet light chamber comprises a viewing port to allow a user to confirm that the lamp is off when attempting to change it.

Finally, in the preferred air sterilization system the blower that is a centrifugal air blower with a high-pressure reverse curve motorized impeller and the air inlet includes a valve for sealing air outside of the system.

In its most basic form, the method of purifying air using a multi-chamber air purification system includes the steps of taking air into the air purification system, testing the air for nuclear, biological and chemical contaminants, mechanically filtering the air; chemically filtering the air; irradiating the air with ultraviolet light; and exhausting purified air from the air purification system. The preferred method includes the step of pre-filtering said air immediately following said step of taking air into the air purification system.

Therefore, it is an aspect of the invention to provide an air purification system that provides human protection from atmospheric contaminants in the event of a nuclear, biological or chemical attack or accident.

It is a further aspect of the invention to provide air purification system that filters air directly from the atmosphere.

It is a further aspect of the invention to provide air purification system that may be effectively operated by batteries.

It is a further aspect of the invention to provide air purification system that includes a means for determining whether contaminants are present within the air entering the system.

It is a further aspect of the invention to provide air purification system that does not require that used chemicals are removed and fresh chemical replenished.

It is a further aspect of the invention to provide air purification system that may be sized to easily fit within the entranceway of a conventional shelter.

It is a further aspect of the invention to provide air purification system that may be sealed to prevent ingress or egress of air from an enclosed space.

It is a further aspect of the invention to provide air purification system that protects against all known strains of bacteria and airborne viruses.

These aspects of the invention are not meant to be exclusive and other features, aspects, and advantages of the present invention will be readily apparent to those of ordinary skill in the art when read in conjunction with the following description, appended claims and accompanying drawings.

DETAILED DESCRIPTION OF THE INVENTION

Figure 1:
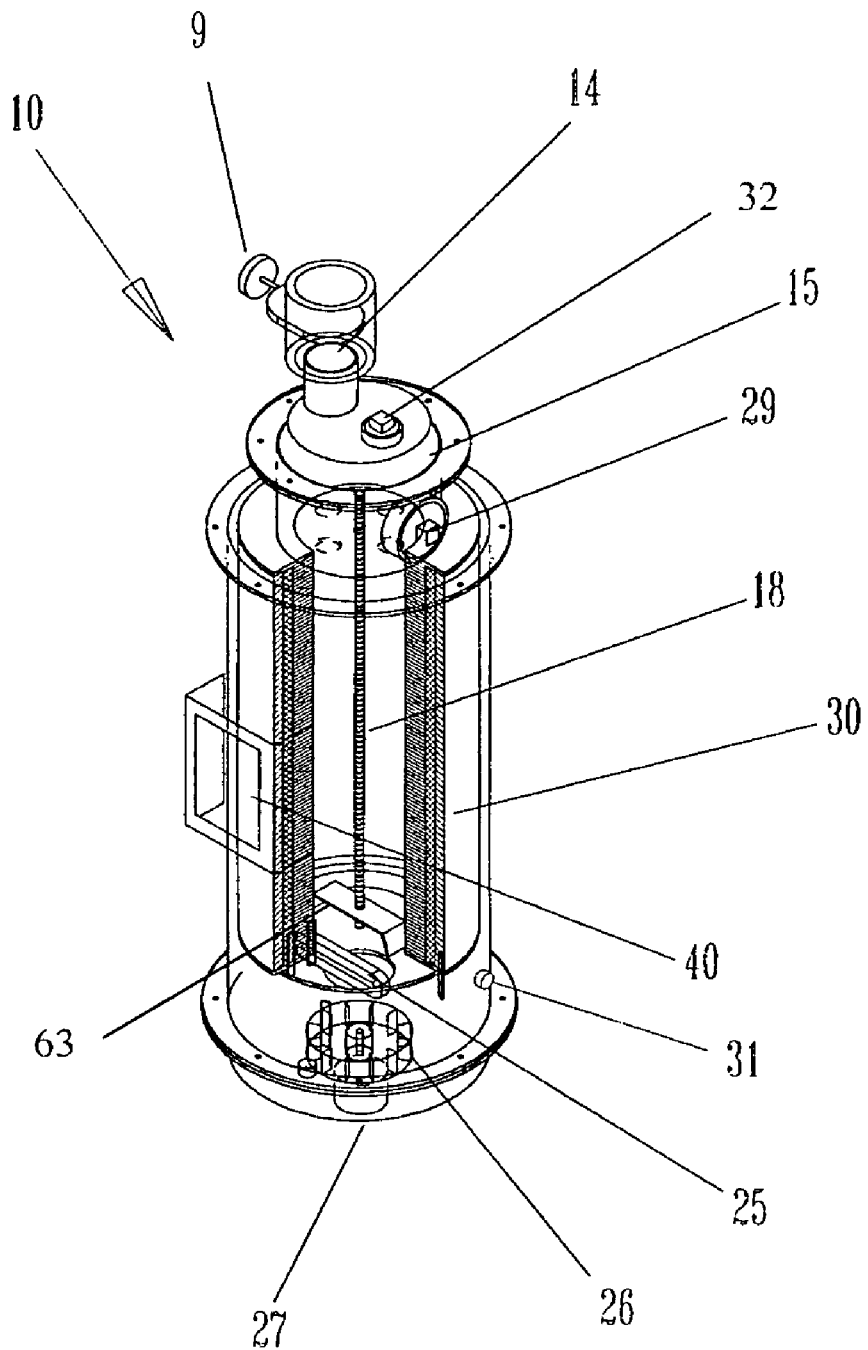
FIG. 1 is a side isometric view of the preferred air purification system of the present invention with a portion cut away to reveal the interior thereof.
Figure 2:
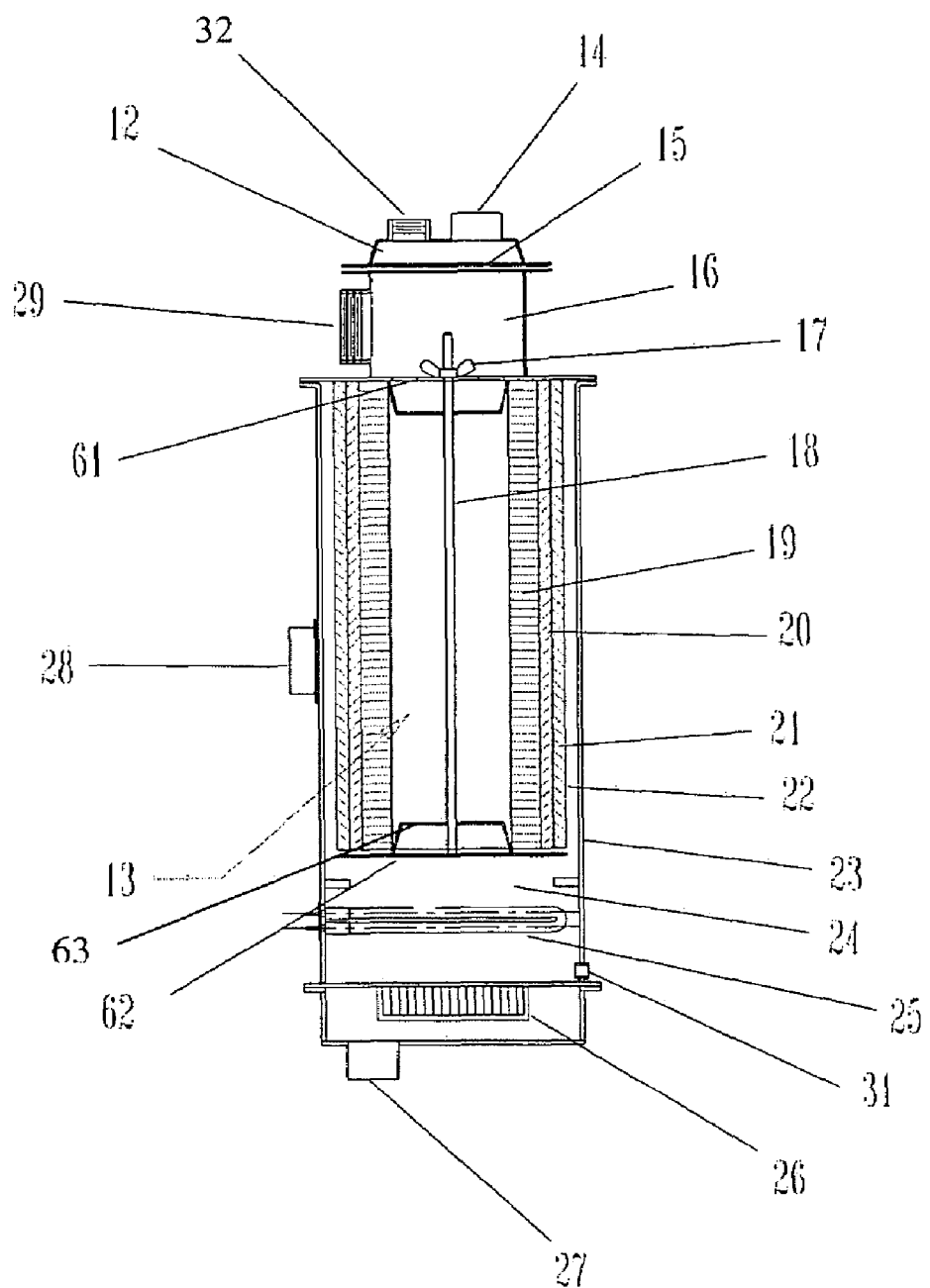
FIG. 2 is a cross sectional view of the preferred air purification system of the present invention.

Referring first to FIGS. 1 and 2, the multi chamber air purification system (MCAS) 10 is a unique multi chamber nuclear, biological and chemical air filtration unit designed to remove or kill all nuclear-biological-chemical agents known. Contaminated air is drawn though a pre-filtering chamber 12, an air test chamber 16, a mechanical and chemical filtration chamber 13, and an ultraviolet light chamber 24, which sterilizes the air that then passes through an air blower 26 and out through an air exhaust 27 which forces the purified air into the shelter (not shown).

Stage 1: Pre-Filter

Air enters the MCAS 10 through an air inlet 14, which is in communication with the environment outside of the shelter. The air inlet 14 preferably includes a valve 9 that allows the MCAS 10 to be sealed from the environment. Air passes through the air inlet 14 into pre-filter chamber 12 that includes a micronic mesh screen 15 to remove large particles in the air that are larger than one hundred and twenty five microns. The pre-filter chamber 12 is preferably removable and the screen 15 is preferably manufactured of stainless steel, which allows it to be washed, greatly extending the life of the next filtration stage. However, the micronic screen may be manufactured of brass or non-metallic materials commonly used in the art to screen large particles. The cover of the filter chamber has a visual inspection port 32, which has two functions. First, by removing the pipe plug, it allows a safe way of inspecting the pre-filter screen 15 to see if it is dirty and restricting the air flow. Second, with a common spray bottle, it allows a way of introducing a spray mist of hypochlorite and water to make the pre-filter screen 15 moist so that contaminated dust does not fly around. Once the pre-filter screen 15 is moist, it can be removed, washed, and replaced.

Stage 2: Air Test Chamber

Under the pre-filter chamber 12 is air test chamber 16, which contains a gas agent test port 29, where the incoming air can be tested for chemical agents. The test port 29 preferably accommodates a standard ARMY M256A test kit (not shown). However, the test port 29 is not intended to be so limited and may be adapted to accommodate other art recognized test kits In the preferred embodiment, a four inch national pipe thread male plug is unscrewed and the test card is placed on the floor of the air test chamber 16. Since the whole MCAS 10 is under negative pressure there is no risk of contamination, although it is suggested that rubber gloves be used. The test port 29 is also a way of accessing the wing nut 17 of the acme rod 18 to allow removal of the filter stem 63, which is attached to acme rod 18 and permanently connected to bottom plate 62, to replace the filter sleeve 30 from the mechanical and chemical filtering chamber 13.

Stage 3: Mechanical and Chemical Filtering

The third chamber is the mechanical and chemical filtering chamber 13, where radioactive particles, some smoke, and biological agents can be removed by using mechanical filtration. The preferred filter chamber 13 includes a housing 23 that houses a highly effective particulate air filter (HEPA filter) 19, which works by a physical straining through a filter sleeve 30; removing dust that is so fine that it is not visible to the human eye. The preferred HEPA filter 19 is a pleated HEPA filter that has 99.99% efficiency in removing particles which are 0.3 microns in diameter (0.000012 inches) and larger. Although biological viruses range from 0.02 to 0.25 microns, they are dispersed or carried by larger aerosol or dust particles, which can usually be removed by physical straining.

Figure 3:
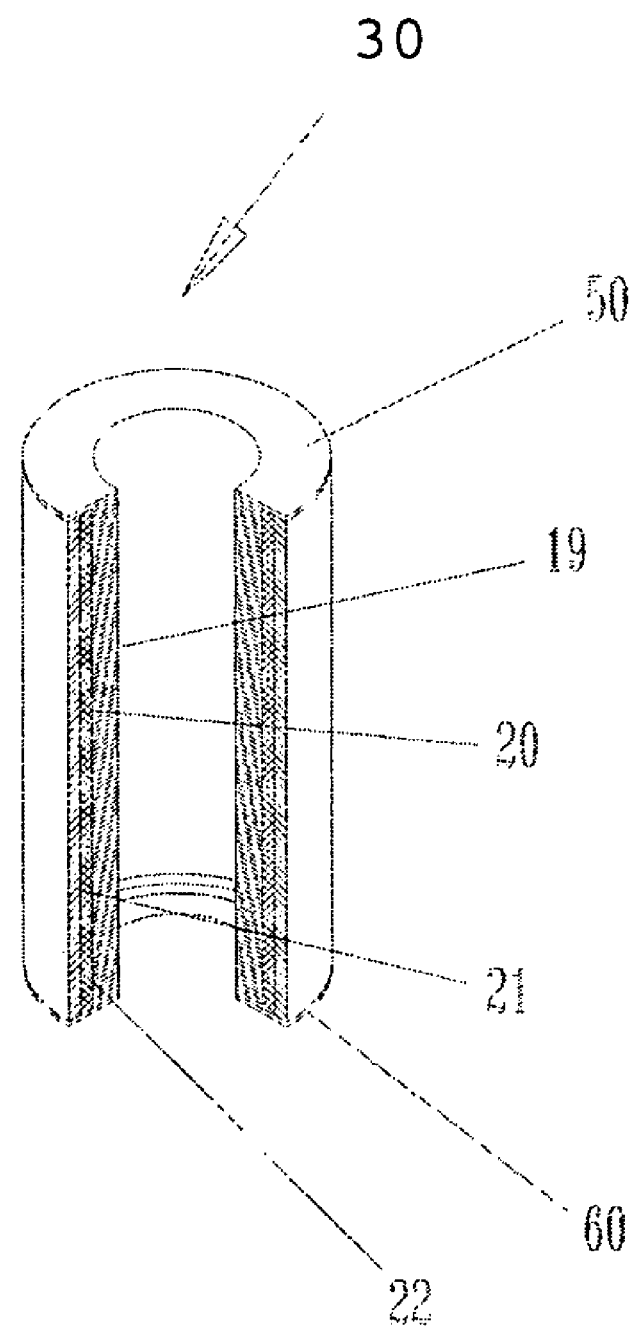
FIG. 3 is a cutaway side isometric view of the preferred filter sleeve of the air purification system of the present invention with a portion cut away to reveal the interior thereof.

Referring now to FIGS. 2 and 3, the filter sleeve 30 is designed to be compressed from each end sealing against the gaskets 50 and 60 commonly composed of neoprene, buna N, or EPDM. The compression is developed by an acme stainless steel rod 18 running down the center of the filter sleeve 30, which sandwiches the filter sleeve 30 between a substantially fixed top plate 61, and a movable bottom plate 62 that is secured to the acme rod 18. A nut 17, preferably a wing nut, is housed in the air test chamber 16 and is threaded onto the acme rod 18 which extends through the top plate 61. Rotating the nut 17 causes the acme rod 18 and attached bottom plate 62 to move upward, forcing the bottom plate 62 up against the bottom of 60 and top 50 of the filter sleeve 30, forming a complete and tight seal.

A mechanical filter, such as a typical HEPA filter 19, is not able to remove radioactive iodine gas. For this contaminant, an impregnated activated carbon filter 20 must be employed. The activated carbon layer 20 purifies the air by processes called physical adsorption which is a chemical attraction.

Physical adsorption is a process where activated carbon is used to perform a physical straining of contaminants, based on the molecular force, much like a coffee filtering process but using a much finer filter. Carbon is used because it has an extremely fine pore structure, much smaller than HEPA filter 19, and contains tremendous surface area. For some types of carbon, a volume of one quart contains a surface area of 9 million square feet. This makes adsorption efficient and practical.

Chemical adsorption is a process where impregnated carbon is used in the activated carbon filter 20. Impregnated carbon has been treated with specific chemicals, which have an affinity to attract and thereby remove specific toxins or gases. There is a specific carbon to remove radioactive iodine gas and the efficiency of removing the contaminant is based on the amount of time the contaminant is in contact with the carbon. This required period of time necessary to remove the contaminant is known as the residence time. Radioactive iodine gas requires a residence time of 0.35 seconds.

Burning forests produce toxic gases such as: nitrogen oxides, benzene gas, toluene gas, and carbon dioxide. Toxic gases produced from burning plastics and industrial chemicals are known as pyrotoxins. These pyrotoxins are: nitric acid gas, chlorine gas, chlorinated dioxin gas, hydrochloric acid gas, acrolein gas, and sulfuric acid gas. These gases would be dangerous primarily in the immediate blast area for a number of days. These toxins can be removed from the fresh air supply using a carbon filter, designed to remove acid gas. The activated carbon layer 20 of filter sleeve 30 is designed to also filter out these acid gases.

The filter sleeve 30 includes two layers of carbons. The first layer consists of an activated carbon layer 20, which removes radioactive iodine gas generated from a nuclear explosion or nuclear power plant accident. This activated carbon layer 20 makes it unnecessary to take Potassium Iodine to block the absorption of radioactive iodine into the human thyroid. Iodine tablets only work if they are taken twenty-four hours in advance of breathing the radioactive iodine gas.

The second layer consists of a chemical warfare agent filter layer 21, which is specifically designed to remove chemical warfare agents. Chemical warfare agent filter layer 21 functions like impregnated carbon in the activated carbon layer 20. The preferred carbon for use in this layer is called "Whetlerite Carbon", meeting military specifications Mil-C-0013724C (EA) Grades 1 to 4, and is used in military blast shelters. This carbon has been impregnated with copper, chromium, and silver to specifically remove: carbon sulfate gas, cyanide gas, phosgene oxime gas, mustard gas, phosgene gas, cyanogen chloride, sarin gas, soman gas, VR-55 gas, VX gas, and other chemical warfare agents. It is extremely efficient, lasts many years, and is very expensive.

The outside filter layer 22 of the filter sleeve 30 is the "post filter". When air is drawn through any carbon filter, some very fine particles of carbon are removed and deposited outside of the filter. Because they are extremely fine, they get into everything just by air movement within the shelter or house; thus, they are easily inhaled. These particles are called "carbon fines" and are contaminated and must be kept within the filter. This is accomplished by using a micronic fabric on the outside filter layer 22 of the filter sleeve 30 to contain the carbon fines within the filter sleeve 30.

Stage 4: Ultraviolet Light Irradiation

The fourth chamber is the ultraviolet light chamber 24, which houses an ultraviolet lamp 25 that emits light of a wavelength and intensity that kills all known biological agents, such a viruses and bacteria. Altantic Ultraviolet Inc. makes a 32 watt U shape germicidal bulb at 254 nm which does not produce ozone and has with a specific ballast 28. Viruses are tiny geometric structures that can only reproduce inside a living cell. They range in size from 0.02 to 0.25 microns. When they are outside a living cell they are dormant but when it enters a host cell, it begins to generate more virus particles. Bacteria are one cell living organisms with an average size of 1 micron that does not need a living host. Many bacteria are beneficial to humans and necessary for the breakdown of organic wastes.

Many viruses and bacteria are so small that they are not able to be filtered physically by the HEPA filter 19 or effectively adsorbed by the activated carbon layer 20 or chemical warfare agent filter layer 21. Virtually all biological warfare agents can be removed by filtering out what they are carried on such as a dust particle or aerosol droplet. Viruses however, are usually in the gaseous state and need to be killed by ultraviolet radiation (UVC) or ultraviolet germicidal irradiation (UVGI) which is an ultraviolet light on the C scale, preferably at a wavelength of 254 nm which does not generate ozone. The amount of energy required to completely kill an organism such as a virus, bacteria, mold, etc is called the "kill energy" which varies with each organism. The ultraviolet lamp 25 under the bottom plate 62 of the filter sleeve 30 develops extremely high kill energy as a result of the air slowing down as it passing through the larger diameter ultraviolet chamber 24, preferably manufactured of stainless steel, which allows more exposure time to assure that the kill rate is absolute. Exposure time is based on light intensity multiplied by time. The exposure imposed on any organism in the MCAS 10 is 11,200 uwsec/cm2. (microwatts/sec/square centimeter)

Ultraviolet radiation does have two dangers. When exposed to bare skin, it will produce a radiation burn, commonly called sunburn, and is also damaging to the human eyes and can result in conjunctivitis, characterized by inflammation of the mucous membranes. When changing the bulbs, the ultraviolet lamp 24 must be turned off to avoid these dangers. On the side of the MCAS 10 is a visual site port 31 to visually verify if the ultraviolet lamp 25 is on. This visual site port 31 is preferably thick enough to prevent any appreciable radiation negatively affecting nearby occupants.

Stage 5: Blower

The blower 26 is preferably a centrifugal air blower with a high pressure reverse curve motorized impeller located at the bottom of the canister to create negative pressure inside the filter canister or housing drawing air through the MCAS 10. This blower 26 sends filtered air into the shelter. If the air leaving the shelter is restricted, the shelter will be positively pressurized, preventing contaminating agents from entering the shelter.

The control panel 40 consists of circuit breaker for the blower 26 and ultraviolet light 25. Each circuit breaker has an indicator light show visually verifying power to the blower 26 and ultraviolet light 25.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. A air sterilization system comprising:
   an air inlet in communication with a source of air;
   an air test chamber in fluid communication with said air inlet;
   a mechanical and chemical filtration chamber in fluid communication with said air test chamber, wherein said mechanical and chemical filtration chamber comprises a filter sleeve comprising a highly effective particulate air filter, an activated carbon layer, a chemical warfare agent filter layer and an outside filter layer manufactured of a material adapted to contain carbon fines within said filter sleeve;
   an ultraviolet light chamber in communication with said mechanical and chemical filtration chamber, wherein said ultraviolet light chamber comprises an ultraviolet lamp disposed therein;
   an air blower in communication with said ultraviolet light chamber; and
   an air exhaust in communication with said air blower.

2. The air sterilization system as claimed in claim 1 further comprising a pre-filtering chamber, wherein said pre-filtering chamber is disposed between said air inlet and said air test chamber and comprises a micronic screen through which air is forced to pass.

3. The air sterilization system as claimed in claim 2 further comprising a screen access port dimensioned to allow said micronic screen to be removed from said pre-filtering chamber.

4. The air sterilization system as claimed in claim 3 wherein said micronic screen is manufactured of stainless steel.

5. The air sterilization system as claimed in claim 1 wherein said air test chamber comprises a test port and a male plug dimensioned to mate with and be removable from said test port.

6. The air sterilization system as claimed in claim 1 wherein said filter sleeve comprises a substantially hollow cylindrical shape having an open top and an open bottom.

7. The air sterilization system as claimed in claim 1 further comprising a filter stem, a bottom plate, an acme rod passing through said filter stem, said filter sleeve and said bottom plate, and a nut threaded onto said acme rod and in communication with one of said filter stem and said bottom plate, wherein said filter sleeve comprises a first gasket in communication with said filter stem and a second gasket in communication with said bottom plate, and wherein said filter sleeve is sealably secured between said filter stem and said bottom plate when said nut is moved downward on said acme rod.

8. The air sterilization system as claimed in claim 6 wherein said highly effective particular air filter of said filter sleeve is a pleated highly effective particular air filter.

9. The air sterilization system as claimed in claim 6 wherein said chemical warfare agent filter layer of said filter sleeve comprises Whetlerite Carbon.

10. The air sterilization system as claimed in claim 6 wherein said outside filter layer of said filter sleeve is manufactured of a micronic fabric material adapted to contain carbon fines within said filter sleeve.

11. The air sterilization system as claimed in claim 1 wherein said ultraviolet lamp is an ultraviolet germicidal irradiation lamp adapted to generate ultraviolet light having a wavelength of 254 nanometers.

12. The air sterilization system as claimed in claim 1 wherein said ultraviolet lamp is dimensioned to slow the air flow as it flows through the ultraviolet light chamber such that said air is exposed to level of kill energy sufficient to kill substantially all biological agents.

13. The air sterilization system as claimed in claim 1 wherein said ultraviolet light chamber comprises a viewing port.

14. The air sterilization system as claimed in claim 1 wherein said blower 26 a centrifugal air blower with a high pressure reverse curve motorized impeller.

15. The air sterilization system as claimed in claim 1 wherein said air inlet comprises a valve for sealing air outside of said system.

16. The air sterilization system as claimed in claim 2 wherein said filter sleeve comprises a substantially hollow cylindrical shape having an open top and an open bottom.

17. The air sterilization system as claimed in claim 2 further comprising a top plate, a bottom plate, an acme rod secured to said bottom plate and passing through said top plate and said filter sleeve, and a nut threaded onto said acme rod and in communication with said top plate;
   wherein said filter sleeve comprises a first gasket in communication with said top plate and a second gasket in communication with said bottom plate; and
   wherein said filter sleeve is sealably secured between said top plate and said bottom plate by rotating said nut such that said acme rod and bottom plate move upward toward said top plate.

18. The air sterilization system as claimed in claim 16 wherein said chemical warfare agent filter layer of said filter sleeve comprises Whetlerite Carbon and said activated carbon filter layer of said filter sleeve comprises activated carbon and impregnated carbon.

19. The air sterilization system as claimed in claim 6 wherein said activated carbon filter layer of said filter sleeve comprises activated carbon and impregnated carbon.

* * * * *